United States Patent [19]
Tsai

[11] Patent Number: 5,876,561
[45] Date of Patent: Mar. 2, 1999

[54] POST DIGESTION TREATMENT OF CELLULOSIC PULP TO MINIMIZE FORMATION OF DIOXIN

[75] Inventor: Ted Yuan Tsai, Harriman, N.Y.

[73] Assignee: International Paper Company, Purchase, N.Y.

[21] Appl. No.: 843,834

[22] Filed: Feb. 28, 1992

[51] Int. Cl.⁶ .............................. D21C 9/02; D21C 9/12; D21C 9/14; D21C 9/153

[52] U.S. Cl. ................................. 162/60; 162/65; 162/89

[58] Field of Search .................................. 162/87, 88, 89, 162/65, 56, 60, 66, 67

[56] References Cited

U.S. PATENT DOCUMENTS

| | | | |
|---|---|---|---|
| 3,655,505 | 4/1972 | Yorston et al. | 162/67 |
| 4,259,149 | 3/1981 | Jaszka et al. | 162/29 |
| 4,595,456 | 6/1986 | Andersson | 162/47 |
| 4,902,381 | 2/1990 | Meredith | 162/65 |
| 4,959,124 | 9/1990 | Tsai | 162/67 |

OTHER PUBLICATIONS

Perkins et al, "Gas Phase Bleaching", *CEP;* Jun. 1976, pp. 51–54. (162–67).

Basta, Jiri, Holtinger, Lillemor, Hook, Jan and Lundren, Per, Reducing Levels of Absorbable Organic Haologens (AOX), TAPPI Journal, pp. 155–160, Apr. 1990.

Technical News Note, "Swedes Investigate Dioxin", Paper Technology, p. 36, Dec./Jan. 1989.

Hise, Ronnie G and Hintz, Harold L., "The Effect of Brownstock Washing on the Formation of Chlorinated Dioxins and Furans During Bleaching", TAPPI Journal, pp. 185–190, Jan. 1990.

Granum, F.; Hasvold, K.; Loras, V. and Soteland, N., "Influence of Bleaching Chemicals and Sequences on Some Properties of Sulphite Pulps", Journal of Pulp and Paper Science, pp. J 25–J 29, Mar. 1984.

*Primary Examiner*—Steven Alvo
*Attorney, Agent, or Firm*—Luedeka, Neely & Graham, P.C.

[57] ABSTRACT

A post-digestion treatment method for cellulosic pulps which reduces the generation of dioxins and other chlorinated organics in the pulp, treatment effluent and/or the paper product produced from the pulp. In the treatment, the pulp, following digestion, is washed with a liquid that is essentially free of dioxins or dioxin precursors and simultaneously adjusted in consistency to at least a medium, and preferably a high consistency. Thereafter, the pulp is contacted with a chlorination agent selected from the group consisting of gaseous chlorine dioxide, gaseous chlorine, and gaseous chlorine dioxide which contains a minor amount of gaseous chlorine.

5 Claims, 1 Drawing Sheet

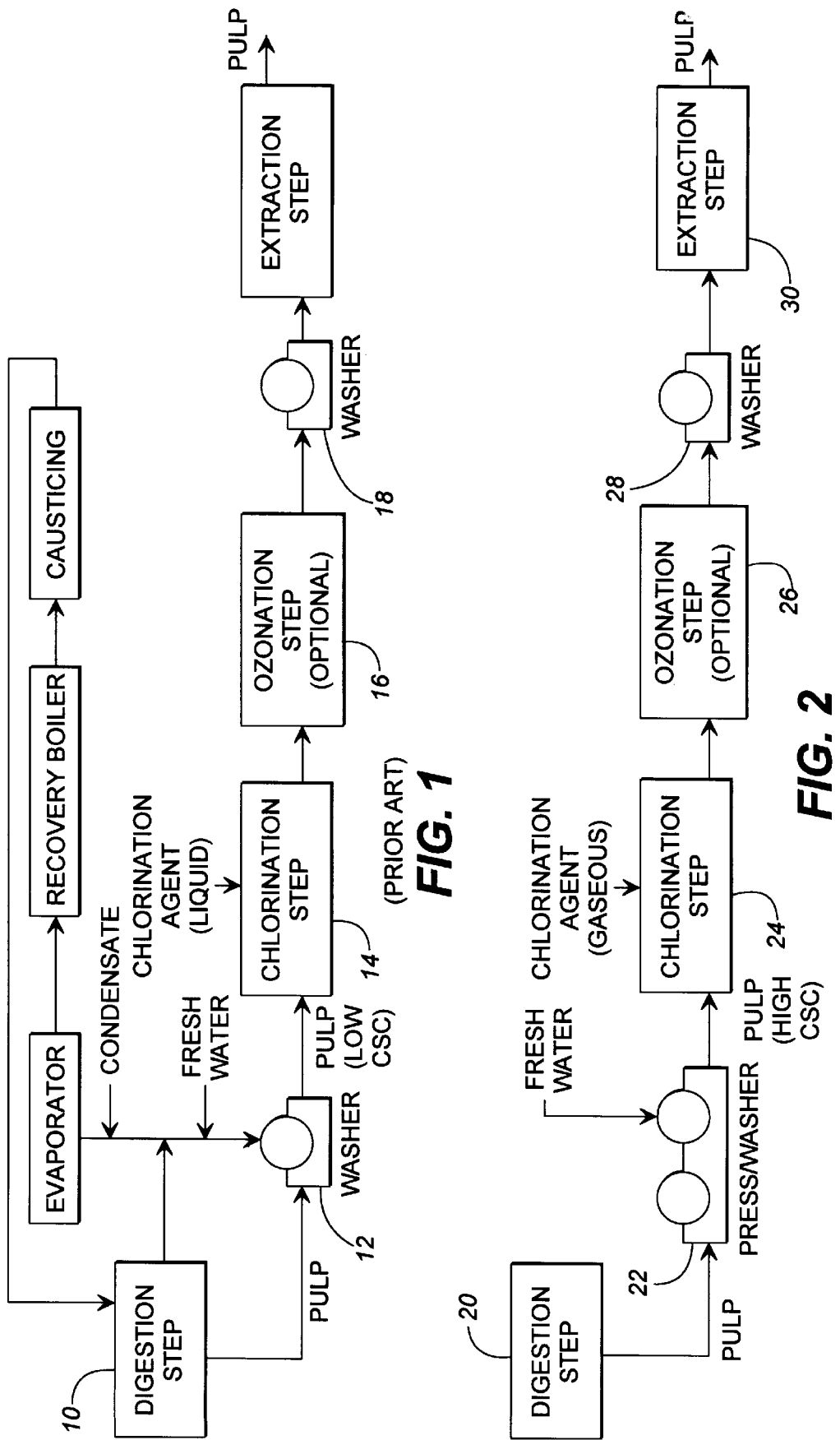

POST DIGESTION TREATMENT OF CELLULOSIC PULP TO MINIMIZE FORMATION OF DIOXIN

This invention relates to the post-digestion treatment of cellulosic pulps, particularly kraft pulps, for the purpose of completing the delignification of the pulp to a target degree of delignification.

In the papermaking process, digested cellulosic (wood) pulp often is treated after digestion to enhance certain of the properties of the pulp. For many end uses, the pulp desirably is substantially delignified, as by the reaction of the lignin in the pulp with various delignification agents such as chlorine, oxygen, ozone, chlorine dioxide, peroxide, etc. The post-digestion delignification most often takes the form of a series of steps, each of which is designed to accomplish a specific task and often to build upon the previous step or prepare the pulp for a subsequent step. At least the initial step of the most commonly used post-digestion treatments, such as chlorination, ozonation, oxygenation, etc. requires that the pulp be adjusted to a consistency of between about ½% and about 10%, on pulp for successful processing.

Also in the prior art, the digested pulp commonly is washed with a wash liquid that is recovered from the digestion and spent-liquor evaporation processes. The recovery procedure commonly involves collection of the condensate from the digester and evaporator and directing a portion of this condensate to a pulp washing step that follows the digestion step. In the prior art, due to flow balance and other considerations, up to about 7 tons of wash liquid is available from the digester and evaporator condensate stream for use as wash liquid. It has been required in the prior art to add to the condensate stream going to the washer, an additional quantity of fresh wash water so as to make up the 12 tons of wash liquid per ton of pulp that is required in the prior art wherein the pulp exiting the washer is required to be of low or medium consistency for subsequent processing.

In the prior art, post-digestion treatments have generated or contributed to the formation of sufficient quantities of dioxins or dioxin precursors as to bring into question the advisability of permitting the use of these treatments without providing for the elimination of dioxins or, if generated, the proper harmless destruction of the same. In particular, the use of chlorine-containing delignification agents have proven most troublesome with respect to the formation of dioxin or dioxin precursors, but these agents remain among the most effective of the known delignification agents, hence it is desired that a post-digestion treatment process be provided which will permit the use of these agents.

"Dioxin" and "dioxin precursors" are terms which at times have been used to refer vaguely or generally to environmentally undesirable chlorinated organic compounds. As used herein, the term "dioxin" or "dioxin precursor", unless indicated otherwise, is intended to refer to one or more of the following:

(1) 2,3,7,8 tetrachloro-dibenzo-p-dioxins (TCDD)
(2) 2,3,7,8 tetrachloro-dibenzofurans (TCDF)
(3) Polychlorinated-dibenzo-p-dioxins (PCDD)
(4) Polychlorinated-dibenzofurans (PCDF)

Other chlorinated organics of related nature are also often found in the pulp, effluent from the post-digestion treatment, and/or in the paper manufactured from the pulp. Thus, "chlorinated organics" is applied herein to these additional environmentally undesirable compounds.

In accordance with the present invention, it has been found that the quantity of dioxin or dioxin precursors associated with the post-digestion treatment of a cellulosic pulp employing a chlorine-containing delignification agent can be limited to non-detectable levels or reduced to less than about 50% of the levels of these compounds known to exist in the prior art. This minimization of dioxin or dioxin precursors is accomplished in the present invention by washing the pulp following its digestion with between about 2 and 4 tons of wash liquid per ton of pulp, employing a wash liquid which is essentially free of dioxin or dioxin precursors, while substantially simultaneously adjusting the consistency of the pulp to a medium or, preferably, a high consistency, e.g. a consistency greater than about 15%, on pulp, and thereafter contacting the enhanced consistency pulp with a chlorination agent selected from the group consisting of gaseous chlorine dioxide, gaseous chlorine, or gaseous chlorine dioxide which contains a minor amount of gaseous chlorine. The chlorinated pulp is thereafter, preferably, subjected to further treatment including at least an alkaline extraction step.

Contrary to the prior art wherein post-digestion treatment of the pulp involves washing of the digested pulp with liquid recovered from the digestion and evaporation process, the present process utilizes a wash liquid which is essentially free of dioxin or dioxin precursors. This wash liquid cannot be the untreated condensate from the digestion and evaporation step. Preferably fresh water is employed. Also contrary to the prior art, the present inventor has found that if the pulp from the digestion step is adjusted to a medium, and preferably a high consistency, it can thereafter be subjected to chlorine-containing delignification agents and gain the benefits therefrom without forming detectable amounts of dioxin or dioxin precursors. This latter desired result is achieved by subjecting the pulp at the medium, and preferably high, consistency to a chlorine-containing delignification agent in a gaseous state. The chlorine-containing delignification agent is selected from the group consisting of gaseous chlorine dioxide, gaseous chlorine, and gaseous chlorine dioxide which contains a minor portion of chlorine, e.g. less than 50% chlorine. In a preferred embodiment, the delignification agent is gaseous chlorine dioxide. When using this preferred delignification agent with either medium or high consistency pulp, it has been found possible to eliminate the formation of detectable amounts of dioxin or dioxin precursors during the chlorination step. When employing gaseous chlorine as the delignification agent, either at medium or high consistency of the pulp, there is a reduction of about 50% of the quantity of dioxin or dioxin precursor formation over that known to exist in the prior art low consistency pulp chlorination processes.

In addition to the reduction in formation of dioxin and dioxin precursors provided by the present invention, there is also accomplished a savings in the quantity of wash liquid required in the initial wash step prior to the chlorination step. More specifically, the present high-consistency chlorination differs from the conventional low to medium consistency processing of the pulp in that the present process requires only between about 2 and 4 tons of wash liquid per ton of pulp as compared to the 12 tons of wash liquid per ton of pulp required by the prior art. This factor eliminates the need for use of the condensate from the digestor and evaporation step and therefore eliminates the introduction of possible dioxin or dioxin precursors that may come from the digestion step.

It is therefore an object of the present invention to provide a post-digestion treatment for cellulosic pulp which employs a chlorine-containing delignification agent and which eliminates or minimizes the formation of dioxin or dioxin precursors.

It is another object of the present invention to provide a post-digestion treatment for cellulosic pulp wherein there is employed a reduced volume of wash liquid in the washing step employed between digestion and chlorination of the pulp.

Other objects and advantages of the invention will be recognized from the following description and claims, and including the drawings.

BRIEF DESCRIPTION OF THE DRAWINGS

FIG. 1 is a schematic diagram of a prior art post-digestion treatment of cellulosic pulp employing a chlorine-containing delignification agent and wherein condensate from the digestor and evaporator is employed in the wash liquid for a washing step that precedes chlorination; and, FIG. 2 is a schematic diagram of a post-digestion treatment of cellulosic pulp embodying various of the features of the present invention.

DETAILED DESCRIPTION OF THE INVENTION

With reference to FIG. 1, there is depicted a prior art post-digestion treatment for cellulosic pulp in which the pulp from a digestion step 10 is fed to a conventional washer 12 wherein the pulp is washed with a wash liquid made up of condensate collected from the digestion and evaporation steps and fresh water. The pulp at low consistency (1%–10%, on pulp) is thereafter fed to a chlorination step 14 where the pulp is contacted with a liquid chlorination agent which serves to react with the lignin of the pulp and render it soluble in alkaline solution. Optionally, the pulp from the chlorination step may be fed to and through an ozonation step 16 wherein further delignification is carried out. The pulp is next passed through a second washer 18 and thence to and through a conventional extraction step. In the extraction step, the pulp is adjusted to an alkaline pH as by the addition of sodium hydroxide to solubilize the chlorinated lignins which may be subsequently removed by washing, etc. as is well known in the art.

In FIG. 2 there is depicted a post-digestion treatment process which embodies various of the features of the present invention. In this depicted embodiment of the present process, pulp from a digestion step 20 is fed to a high efficiency washer or press 22 wherein the pulp is washed with fresh water and the pulp is adjusted to a high consistency (e.g. 15–40%, on pulp). This high consistency pulp is fed to a chlorination step 24 where the pulp is contacted with a gaseous chlorine-containing delignification agent. Thereafter, the pulp may be processed through an optional ozonation step 26, through a conventional washer 28, and a conventional extraction step 30.

In the first washing step for the pulp following the digestion step, to wash the pulp and establish its consistency to a medium consistency (10–15%, on pulp) approximately 12 tons of wash liquid is required for each ton of pulp processed. In the prior art (FIG. 1), about 8 tons of this wash liquid is supplied from the condensate from the pulp digestion and evaporation steps and about 4 tons of fresh water is added to the condensate stream. In accordance with the present process, the consistency of the pulp in the first washer/press is adjusted to a high consistency, preferably between about 15% and 40%. By this action, the present inventor has reduced the required volume of wash liquid to between about 2 and 4 tons per ton of pulp and eliminated the need for using the condensate in the wash liquid. From the evidence in hand, it appears that this has eliminated a considerable source of dioxin or dioxin precursors. Further, by processing the pulp at high consistency through the chlorination step employing gaseous chlorine dioxide, gaseous chlorine, or a mixture of gaseous chlorine dioxide and chlorine wherein the gaseous chlorine is a minor portion of the mixture, it further appears that the chlorine preferentially reacts with the lignin, as opposed to reaction with other of the components of the pulp, and thereby forms few, if any, dioxins or dioxin precursors. The overall result of the present process, when using gaseous chlorine dioxide in the chlorination step, is to essentially eliminate the formation of dioxin or dioxin precursors. When using gaseous chlorine or a gaseous mixture of chlorine dioxide and chlorine, the result is a reduction of about 50% in the formation of dioxin or dioxin precursors, compared to the prior art.

Table I hereinbelow shows the formation of dioxin or dioxin precursors when treating cellulosic pulp (Southern Pine kraft pulp of Kappa No. 30.3 and a viscosity of 35.0 cP) in accordance with several prior art bleaching sequences. Notably, each of these sequences produces significant quantities of PCDDs and PCDFs. The D→CE$_{o+p}$D (control) sequence did not produce detectable amounts of 2,3,7,8 TCDD in the pulp itself, but did produce this dioxin in the filtrate from the process. This sequence further produced significant quantities of 2,3,7,8 TCDF. Each of the sequences produced quantities of other PCDDs and other PCDFs.

TABLE I

| | | PCDDs and PCDFs Generated in Low Chlorination Bleaching Processes[1] Unit: ppt on pulp) | | | |
|---|---|---|---|---|---|
| Bleaching Sequence | | 2,3,7,8 TCDD | 2,3,7,8 TCDF | Other PCDDs | Other PCDFs |
| D→CE$_{o+p}$D (Control) | Pulp | ND | 2.48 | OCDD (172.7) Hepta CDD (1.75) | Tetra CDF (14.4) |
| | Filtrate | 2.48 | 30.3 | Other TCDD (33.5) Penta CDD (52.1) Hexa CDD (36.1) Hepta CDD (3.3) | Di CDF (1.24) Tri CDF (20.1) Tetra CDF (6.9) Penta CDF (57.0) Hexa CDF (13.0) |
| DZE$_o$D | Pulp | ND | ND | OCDD (33.17) | Tri CDF (15.1) |
| | Filtrate | ND | ND | OCDD (10.37) | Penta CDF (0.97) |

TABLE I-continued

PCDDs and PCDFs Generated in
Low Chlorination Bleaching Processes[1]
Unit: ppt on pulp)

| Bleaching Sequence | | 2,3,7,8 TCDD | 2,3,7,8 TCDF | Other PCDDs | Other PCDFs |
|---|---|---|---|---|---|
| DE₀DP | Pulp | ND | 1.762 | OCDD (64.4) | Tri CDF (21.3) |
|  | Filtrate | ND | ND | OCDD (90.9) | Penta CDF (1.44) |
| ODOD | Pulp | ND | ND | OCDD (59.5) | Tri CDF (15.9) |
|  | Filtrate | ND | ND | OCDD (21.8) | Penta CDF (0.89) |
| ODZE₀D | Pulp | ND | ND | OCDD (29.6) | Tri CDF (11.3) |

Remarks:
[1](a) Southern Pine kraft pulp, with 1% reject from cooking, Kappa = 30.3, pulp viscosity = 35.0 cP.
(b) Oxygen delignified pulp, Kappa = 15.0, pulp viscosity = 27.7 cP.
(c) First chlorination stage was conducted at 45° C. for 30 minutes.
(d) Eo, $E_{o+p}$ was conducted in Quantum Reactor at 10% CSC, 75° C. for 1 hour at 45 psig $O_2$ pressure, gradually reduced to 0 psig.
(e) 0 was conducted at 90° C. for 1 hour at 80 psig $O_2$ pressure.
(f) Final D stage was conducted at 10% CSC, 70° C. for 2.5 hours.
(g) P stage was conducted at 70° C. for 1 hour.

Table II presents the results of testing of pulp treated in accordance with the claimed process, employing high consistency pulp and gaseous chlorine dioxide, and shows that the process produced no detectable amounts of any of the dioxin or dioxin precursors listed.

TABLE II

| Product | Concentration (ppt) | Detection Limit |
|---|---|---|
| 2378-TCDD | ND[1] | 0.3 |
| 12378-Penta CDD | ND | 0.3 |
| 123478-Hexa CDD | ND | 0.6 |
| 123678-Hexa CDD | ND | 0.5 |
| 123789-Hexa CDD | ND | 0.6 |
| 1234678-Hepta CDD | ND | 0.6 |
| OCDD | ND | 4.3 |
| 2378-TCDF | ND | 0.3 |
| 12378-Penta CDF | ND | 0.2 |
| 23478-Penta CDF | ND | 0.1 |
| 123478-Hexa CDF | ND | 0.5 |
| 123678-Hexa CDF | ND | 0.4 |
| 234678-Hexa CDF | ND | 0.5 |
| 123789-Hexa CDF | ND | 0.7 |
| 1234678-Hepta CDF | ND | 0.4 |
| 1234789-Hepta CDF | ND | 0.6 |
| OCDF | ND | 0.4 |
| TOTAL TCDD | ND | 1.4 |
| TOTAL Penta CDD | ND | 0.3 |
| TOTAL Hexa CDD | ND | 0.6 |
| TOTAL Hepta CDD | ND | 0.6 |
| TOTAL TCDF | ND | 0.39 |
| TOTAL Penta CDF | ND | 0.1 |
| TOTAL Hexa CDF | ND | 0.5 |
| TOTAL Hepta CDF | ND | 0.5 |

[1]Not Detectable

Tables III A–C show the results of dioxin analysis of softwood pulp when processed in accordance with the present invention.

TABLE IIIA

DIOXIN ANALYSIS RESULTS FOR GAS-PHASE CHLORINATION

| | High csc (29.7%) | 3.5% csc, Conventional Cl₂ Water | | High (31.14%) csc, Cl₂ Water |
|---|---|---|---|---|
| Example No. | | | | |
| | 1 | 2 | 3 | 4 |
| P. No. | | | | |
| | 8.9 | 8.8 | 8.1 | 11.0 |
| | ClO₂ Pulp | Cl₂ Pulp | Cl₂ Pulp | Cl₂ Filtrate | Cl₂ Pulp |
| 2378-TCDD | ND | 15.9 | 30.2 | ND | ND |
| 12378-PeCDD | ND | 2.9 | 4.4 | 0.07 | ND |
| 123478-HzCDD | ND | 17.8 | 2.2 | 0.02 | ND |
| 123678-HxCDD | ND | 5.0 | 5.2 | 0.06 | ND |
| 123789-HxCDD | ND | 1.6 | 20.7 | 0.15 | ND |
| 1235678-HpCDD | ND | 7.1 | 12.6 | ND | ND |
| OCDD | ND | 4.3 | 11.7 | ND | ND |
| 2378-TCDF | ND | 160 | 316 | 6.3 | ND |
| 12378-PeCDF | ND | 0.63 | 1.3 | 1.8 | ND |
| 23478-PeCDF | ND | 0.80 | 1.2 | ND | ND |
| 123478-HxCDF | ND | ND | ND | ND | ND |
| 123678-HxCDF | ND | ND | ND | ND | ND |
| 234678-HxCDF | ND | ND | ND | 0.49 | ND |
| 123789-HpCDF | ND | ND | 0.23 | ND | ND |
| 1234678-HpCDF | ND | 0.49 | ND | 0.07 | ND |
| 1234789-HpCDF | ND | ND | ND | ND | ND |
| OCDF | ND | ND | ND | ND | ND |
| Total TCDD | ND | 21.9 | 36.4 | 0.34 | 3.9 |
| Total PeCDD | ND | 23.9 | 40.8 | 1.8 | 2.4 |
| Total HxCDD | ND | 40.7 | 52.7 | 0.97 | ND |
| Total HpCDD | ND | 10.4 | 19.0 | 0.06 | ND |
| Total TCDF | ND | 230 | 544 | 6.8 | 4.1 |
| Total PeCDF | ND | 30.5 | 24.3 | 10.7 | 0.67 |
| Total HxCDF | ND | ND | 4.3 | 1.0 | 0.28 |
| Total HpCDF | ND | 0.56 | ND | 0.13 | ND |

Notes:
Brownstock: Pine Bluff softwood pulp, Kappa =25.5, viscosity = 27.4 cP, high csc, Cl₂ water, indicates Cl₂ from Cl₂ water.
T = tetra -
Pe = penta -
Hx = hexa -
Hp = hepta -
O = octa -

TABLE IIIB

DIOXIN ANALYSIS RESULTS FOR GAS-PHASE CHLORINATION

| | 3.5% csc Cl$_2$, On-site Gen. | | Conventional Cl$_2$ (3..5%) csc, Cl$_2$ Water | |
|---|---|---|---|---|
| Example No. | 8 | | 9 | |
| P. No. | 12.3 | | 12.3 | |
| | Cl$_2$ Pulp | Cl$_2$ Filtrate | Cl$_2$ Pulp | Cl$_2$ Filtrate |
| 2378-TCDD | 1.1 | ND | ND | ND |
| 12378-PeCDD | 0.88 | ND | 2.4 | 0.27 |
| 123478-HxCDD | ND | 0.34 | ND | 0.21 |
| 123678-HxCDD | ND | 0.12 | ND | 0.74 |
| 123789-HxCDD | ND | 0.07 | 4.8 | 0.22 |
| 1235678-HpCDD | ND | 0.11 | 2.2 | 0.27 |
| OCDD | ND | ND | 7.2 | ND |
| 2378-TCDF | 9.8 | 0.39 | 20.4 | 1.3 |
| 12378-PeCDF | ND | ND | ND | ND |
| 23478-PeCDF | ND | ND | ND | ND |
| 123478-HxCDF | ND | ND | ND | ND |
| 123678-HxCDF | ND | ND | ND | ND |
| 234678-HxCDF | ND | ND | ND | ND |
| 123789-HpCDF | ND | ND | ND | ND |
| 1234678-HpCDF | ND | 0.01 | ND | 0.02 |
| 1234789-HpCDF | ND | ND | ND | ND |
| OCDF | ND | ND | ND | ND |
| Total TCDD | 10.1 | 1.7 | 15.6 | 1.9 |
| Total PeCDD | 9.7 | 1.5 | 19.1 | 1.9 |
| Total HxCDD | 3.7 | 0.65 | 12.8 | 1.5 |
| Total HpCDD | ND | 0.11 | 2.2 | 0.27 |
| Total TCDF | 18.5 | 0.76 | 25.5 | 1.8 |
| Total PeCDF | 4.1 | 0.85 | 4.6 | 2.2 |
| Total HxCDF | 0.51 | 0.007 | ND | 0.03 |
| Total HpCDF | ND | 0.02 | ND | 0.02 |

Note: Pine Bluff brown stock, Kappa = 29.6, viscosity = 33.2 cP.

TABLE IIIC

DIOXIN ANALYSIS RESULTS FOR GAS-PHASE CHLORINATION

| | High csc (28.9%) ClO$_2$, On-site Gen. | | Gas Phase Low csc (3.5%) ClO$_2$, On-site Gen. | | Conventional (3.5% csc) ClO$_2$, On-site Gen. Water | | ClO$_2$ Water Multi-Addition (6) | |
|---|---|---|---|---|---|---|---|---|
| Example No. | 10 | | 11 | | 12 | | 13 | |
| P. No. | 9.9 | | 11.3 | | 11.3 | | 12.1 | |
| | ClO$_2$ Pulp | ClO$_2$ Filtrate | ClO$_2$ Pulp | ClO$_2$ Filtrate | ClO$_2$ Pulp | ClO$_2$ Filtrate | ClO$_2$ Pulp | ClO$_2$ Filtrate |
| 2378-TCDD | ND | ND | ND | ND | ND | ND | ND | ND |
| 12378-PeCDD | ND | ND | ND | ND | ND | ND | ND | ND |
| 123478-HxCDD | ND | ND | ND | ND | ND | ND | ND | ND |
| 123678-HxCDD | ND | ND | ND | ND | ND | ND | ND | ND |
| 123789-HxCDD | ND | ND | ND | ND | ND | ND | ND | ND |
| 1235678-HpCDD | ND | ND | ND | ND | ND | ND | ND | ND |
| OCDD | ND | 0.07 | 7.7 | 0.56 | 6.5 | 0.82 | ND | 0.36 |
| 2378-TCDF | ND | ND | ND | 0.04 | ND | ND | ND | ND |

TABLE IIIC-continued

| | | | | | | | | |
|---|---|---|---|---|---|---|---|---|
| 12378-PeCDF | ND | ND | ND | ND | ND | ND | ND | ND |
| 23478-PeCDF | ND | ND | ND | ND | ND | ND | ND | ND |
| 123478-HxCDF | ND | ND | ND | ND | ND | ND | ND | ND |
| 123678-HxCDF | ND | ND | ND | ND | ND | ND | ND | ND |
| 234678-HxCDF | ND | ND | ND | ND | ND | ND | ND | ND |
| 123789-HpCDF | ND | ND | ND | ND | ND | ND | ND | ND |
| 1234678-HpCDF | ND | ND | ND | ND | ND | ND | ND | ND |
| 1234789-HpCDF | ND | ND | ND | ND | ND | ND | ND | ND |
| OCDF | ND | ND | ND | ND | ND | ND | ND | ND |
| Total TCDD | ND | ND | ND | 0.02 | ND | ND | ND | ND |
| Total PeCDD | ND | ND | ND | 0.008 | ND | ND | ND | ND |
| Total HxCDD | ND | ND | ND | ND | ND | ND | 0.74 | ND |
| Total HpCDD | ND | ND | ND | 0.01 | 1.9 | ND | 1.9 | ND |
| Total TCDF | ND | ND | ND | 0.05 | ND | ND | ND | ND |
| Total PeCDF | ND | ND | ND | 0.05 | ND | ND | ND | ND |
| Total HxCDF | ND | ND | ND | ND | ND | 0.02 | ND | 0.02 |
| Total HpCDF | ND | ND | ND | ND | ND | 0.02 | ND | ND |

Note: Pine Bluff brown stock, Kappa = 29.6, viscosity = 33.2 cP.

With reference to Tables III A–C, Example 1 in which there was gas-phase, high consistency chlorination with chlorine dioxide, there were no detectable dioxin in the chlorinated pulp at a normal chlorinated pulp of Permanganate No. (P.No.) of 8.9. High-consistency gas-phase chlorination with chlorine (Example 2—$Cl_2$ water) generated only about 50–60% of the dioxins found in conventional chlorinated pulp (Example 3). Example 4 shows that a high-consistency gas-phase chlorine stage at a low chlorination factor produces nondetectable levels of tetrachlorodibenzodioxins (2,3,7,8-TCDD) and tetrachloro-dibenzofurans (2,3,7,8-TCDF).

Table IIIB illustrates the results of gas-phase chlorine delignification wherein the chlorine gas was generated from sodium chloride and manganese oxide on site. Examples 8 and 9 show the results from the same degrees of delignification with a low-consistency gas-phase reaction and conventional low consistency chlorine bleaching. Comparison of this invention with a conventional low-consistency chlorine stage (Example 9) shows that 40–50% less dioxins are formed.

Table IIIC lists the results of gas-phase chlorine dioxide delignification. Again, high-consistency gas-phase chlorine dioxide shows clean pulp (Example 10). Low-consistency gas-phase delignification with chlorine dioxide generated trace amount of highly chlorinated dioxins (Example 11), similar to the dioxins generated in a conventional chlorine dioxide delignification process (Example 12).

Another benefit of using high-consistency gas-phase chlorine dioxide treatment of the pulp is that this embodiment makes it become optional to include an ozonation step to achieve target delignification.

What is claimed is:

1. In the delignification of digested chemical cellulosic pulps wherein the pulp is subjected to an initial chlorination stage followed by one of more further stages in which the delignification process is continued to effect a target delignification of the pulp, the improvement for producing a bleached pulp which is essentially free of detectable dioxins, comprising the steps of washing said pulp, following digestion thereof and prior to the initial chlorination step, with a quantity of between about 2 and about 4 tons per ton of pulp, of a wash water which is essentially free of dioxins or dioxin precursors, to thereby effectively eliminate from the digested pulp those dioxins or dioxin precursors which might be present in the liquor of the digested pulp and to establish the consistency of the pulp, prior to the initial chlorination step, to between about 15% and about 40%, thereafter, prior to any other treatment of the pulp, contacting said pulp with a chlorination agent selected from the group consisting of gaseous chlorine dioxide, gaseous chlorine or gaseous chlorine dioxide which contains a minor portion of chlorine, and thereafter processing said chlorinated pulp through at least an alkaline extraction stage, wherein said treated pulp is substantially free of detectable amounts of dioxins.

2. The improvement of claim 1 wherein said pulp is a kraft cellulosic pulp.

3. The improvement of claim 1 wherein said chlorination agent is gaseous chlorine dioxide.

4. The improvement of claim 1 wherein said chlorination agent is a mixture of gaseous chlorine dioxide and gaseous chlorine and wherein said gaseous chlorine comprises less than 50% of said mixture.

5. The improvement of claim 1 and including an ozonation step following said chlorination step and preceding said extraction step.

* * * * *